United States Patent [19]

Cerri et al.

[11] Patent Number: 5,073,663

[45] Date of Patent: Dec. 17, 1991

[54] INCREASING THE LEVEL OF 2-METHYL-2-BUTENE IN ISOAMYLENE

[75] Inventors: Gustavo Cerri, Boonton; Robert C. Michaelson, Kinnelon, both of N.J.

[73] Assignee: Exxon Chemical Patents Inc., Linden, N.J.

[21] Appl. No.: 472,844

[22] Filed: Jan. 31, 1990

Related U.S. Application Data

[63] Continuation of Ser. No. 103,287, Oct. 1, 1987, abandoned.

[51] Int. Cl.$^5$ .............................................. C07C 5/23
[52] U.S. Cl. .................................... 585/668; 585/664; 585/669; 585/802; 203/99; 203/DIG. 19
[58] Field of Search ............... 585/664, 668, 669, 802; 203/99, DIG. 19

[56] References Cited

U.S. PATENT DOCUMENTS

| | | | |
|---|---|---|---|
| 3,151,179 | 9/1964 | Kennedy et al. | 585/668 |
| 3,236,908 | 2/1966 | Sanford et al. | |
| 3,272,887 | 9/1966 | Pitkethly et al. | 585/664 |
| 3,293,317 | 12/1966 | Whitney | 585/664 |
| 3,408,266 | 10/1968 | Ward | 203/99 |
| 3,467,727 | 9/1969 | Kahn | 585/664 |
| 3,920,765 | 11/1975 | Frech et al. | 585/664 |
| 4,013,521 | 3/1977 | Scott | 203/DIG. 19 |
| 4,104,321 | 8/1978 | Ward | 585/671 |
| 4,254,290 | 3/1981 | Chambers et al. | |
| 4,320,232 | 3/1982 | Volkamer et al. | |
| 4,334,964 | 6/1982 | Prezelj et al. | 203/DIG. 19 |
| 4,398,051 | 8/1983 | Araki et al. | |
| 4,447,668 | 5/1984 | Smith, Jr. et al. | |
| 4,691,073 | 9/1987 | Michaelson. | |

FOREIGN PATENT DOCUMENTS 0123338 10/1984 European Pat. Off. .
0644767 1/1979 U.S.S.R. .
1173128 12/1969 United Kingdom .

Primary Examiner—Patrick P. Garvin
Assistant Examiner—E. D. Irzinski
Attorney, Agent, or Firm—Edward F. Sherer

[57] ABSTRACT

A method for increasing the ratio of 2-methyl-2-butene (2MB2) to 2-methyl-1-butene (2MB1) in isoamylenes involves fractionating a feedstream containing tertiary amyl methyl ether (TAME) and isoamylenes including 2MB2 and 2MB1 in a ratio of about 2:1 to effect a separation between an overhead hydrocarbon fraction of isoamylenes including 2MB2 and 2MB1 in a ratio of about 1:1, a bottoms fraction including TAME, and a sidestream hydrocarbon fraction consisting essentially of isoamylenes including 2MB2 and 2MB1 in a ratio of about 6 to 12:1, recovering the sidestream hydrocarbon fraction, and recycling the overhead hydrocarbon fraction of isoamylenes to form a mixture which is subsequently reacted to form the feedstream. Prior to fractionation, the feedstream is formed by passing isoamylene, and optionally TAME, in a vapor phase over an ether cracking catalyst which isomerizes isoamylene and converts 2MB1 to 2MB2, i.e., the feedstream for fractionating, which contains 2MB2 and 2MB1 in a ratio of 2 to 5:1. A method for converting 2-methyl-1-butene to 2-methyl-2-butene which may be used to form the feedstream for fractionating involves providing a hydrocarbon stream comprising isoamylenes including 2MB1 and 2MB2 in a ratio of within the range of 1:1 to 5, adding about TAME to the isoamylenes to form a mixture which is passed in the liquid phase at a temperature and a LHSV which favors isomerization over an acidic ion exchange resin catalyst to produce a reaction product including 2MB1, 2MB2 in a ratio of 1:6 to 12, and TAME.

31 Claims, 1 Drawing Sheet

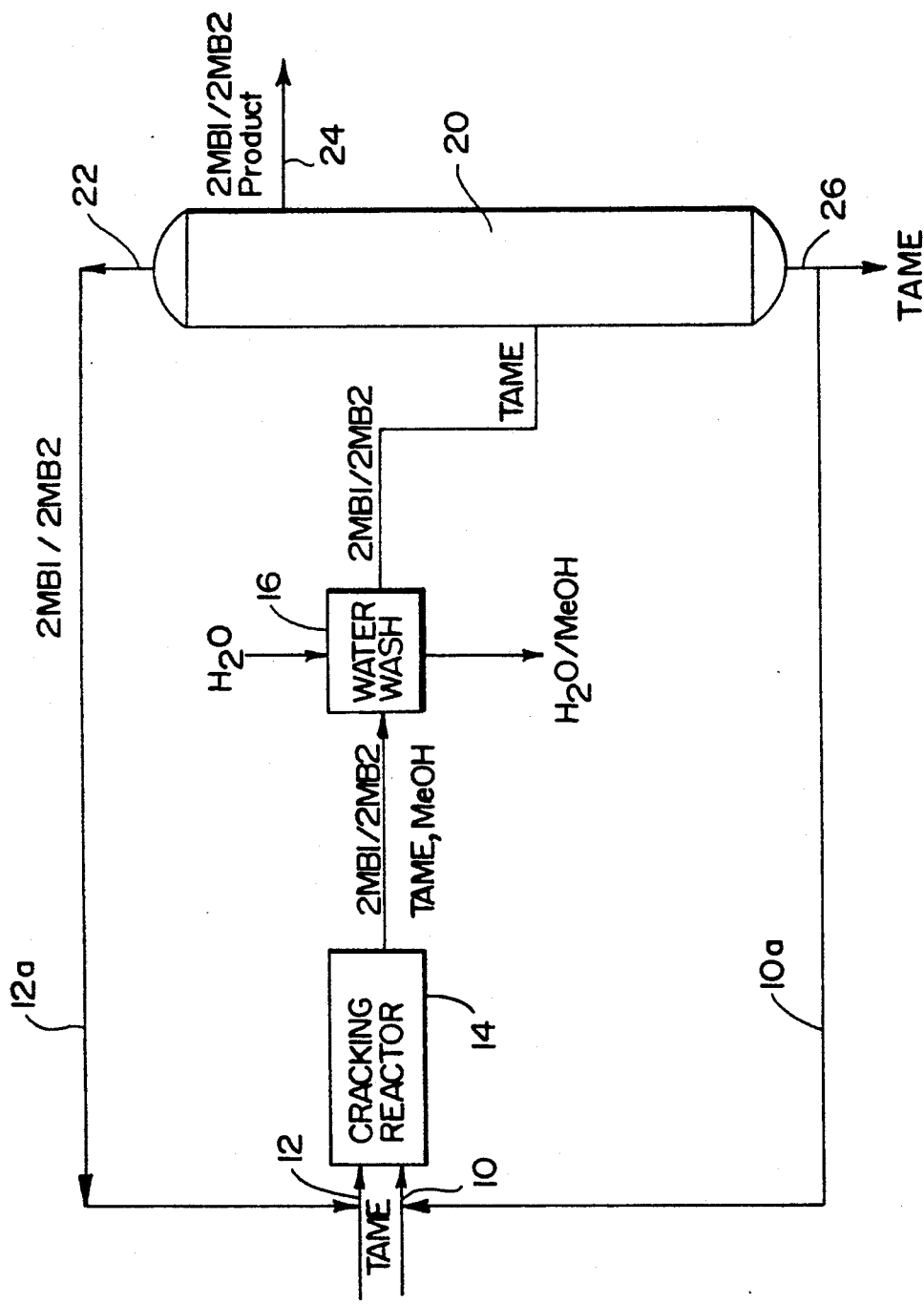

INCREASING THE LEVEL OF 2-METHYL-2-BUTENE IN ISOAMYLENE

This is a continuation of application Ser. No. 103,287, filed Oct. 1, 1987, now abandoned.

BACKGROUND OF THE INVENTION

1. Field of the Invention

The present invention relates to methods for increasing the level of 2-methyl-2- butene in isoamylene, and particularly for converting 2-methyl-1-butene isoamylene into 2-methyl-2-butene isoamylene.

2. Discussion of Background and Material Information

Isoamylene is a component of a $C_5$ refinery stream. The $C_5$ portion of such hydrocarbon streams typically contain at least two isoamylene monomers, i.e., 2-methyl-1-butene and 2-methyl-2-butene in a weight ratio of about 1:1 to about 1:4, and most often about 1:2, respectively.

The separation of isoamylene from other $C_5$ components by fractionation is somewhat difficult because of the closeness of their boiling points, i.e., less than about 10° F. for many of these components. In order to recover the isoamylene content of such a mixture by conventional fractionation, a plurality of steps, for example as disclosed in U.S. Pat. No. 3,236,908, are typically reqired. Each of the fractionations resulting from the multi-step process, however, must be subjected to a further separation of components boiling within a relatively narrow range which requires the employment of complex and expensive equipment.

U.S. Pat. No. 3,236,908, SANFORD et al., attempt to obviate the need for such complex and expensive fractionation equipment by providing a method for producing isoamylene, which is predominantly 2-methyl-2-butene, from the 2-methyl-1-butene present in catalytic gasoline in which a liquid-phase, ambient-temperature, selected isomerization step is used. In their process, the effluent from a catalytic cracking of gas oil is fractionated to produce an overhead fraction consisting essentially of 2-methyl-1-butene and lower boiling $C_5$ hydrocarbons substantially free of higher boiling materials. The fraction thus obtained is then admixed with sulfuric acid of from 60 to 70% by weight concentration with respect to water in order to isomerize 2-methyl-1-butene to 2-methyl-2-butene. The sulfuric acid phase is separated from the hydrocarbon phase and the hydrocarbon phase is then fractionated to recover 2-methyl-2-butene as product.

U.S. Pat. No. 4,447,668, SMITH, Jr. et al., are directed to a method for producing high purity tertiary $C_4$ and $C_5$ olefins by the disassociation of corresponding alkyl ethers and the subsequent dimerization of the olefins to produce high purity dimers thereof. In one embodiment of their process, a feed stream of $C_1$ through $C_6$ alkyl tertiary amyl ether is vaporized and a feed stream in a vaporized state is passed through a fixed bed cationic acidic exchange resin whereby the ether is at least partially disassociated and the disassociation product stream from the catalyst bed contains isoamylene, alcohol corresponding to the alkyl radical and unreacted alcohol tertiary amyl ether. The alcohol is then removed from the disassociation product stream prior to fractionating the condensed stream, which is predominantly isoamylene and unreacted ether feed, to recover isoamylene.

In addition to the foregoing, a number of other methods have been proposed for producing tertiary olefins from alkyl tert-alkyl ethers using various catalysts.

For example, U.S. Pat. No. 4,398,051 uses aluminum compounds supported on silica or other carriers. U.S. Pat. No. 4,320,232 employs phosphoric acid on various supports. British Patent No. 1,173,128 uses metal-containing weakly acidic components on a carrier of $20M^2/gm$ surface area. U.S. Pat. No. 4,398,051 attempts to produce tertiary olefins from alkyl tert-alkyl ethers utilizing carriers alone in the decomposition of methyl tertiary butyl ether. To this end, U.S. Pat. No. 4,254,290 utilizes $H_2SO_4$-treated clay in the decomposition of t-alkyl ether-alkynols.

U.S. Pat. No. 4,691,073, MICHAELSON discovered that high purity olefins are obtainable in extremely high yields over a sustained period by bringing alkyl tert-alkyl ethers into contact with a specified catalyst, i.e, clays treated with hydrofluoric acid and/or hydrochloric acid.

S.U. 644,767, CHAPLITS, is directed to obtaining increased yields of 2-methyl-2-butene by isomerization of 2-methyl-1-butene in the presence of a catalyst composed of a moulded sulpho-cation exchange resin with a thermoplatic material, such as polypropylene and polyethylene, in the presence of methyl-tert-amyl ether tert-amyl alcohol, ethyl alcohol acetone or mixtures thereof, used as 5–10% by wt. of the initial material at a temperature between 60°–80° C., and preferably 70°–80° C., and a pressure of 2.5–4.5 atmospheres.

It is known that tertiary olefins may be prepared by reacting them selectively from petroleum feeds with a primary alcohol in the presence of an acid catalyst to produce the corresponding alkyl tert alkyl ethers. Such alkyl tert-alkyl ethers may then be separated and subsequently decomposed back to the tertiary olefins and the primary alcohol.

For example, European Patent Application No. 123,338, GROENEVELD, is directed to the process for preparation of methyl tertiary butyl ether (MTBE) by reacting isobutene with methanol in the presence of an acid catalyst to yield MTBE followed by conversion of normal butenes present in the hydrocarbon flow to isobutene followed by passing the mixture thus obtained to a reaction zone to form MTBE.

SUMMARY OF THE INVENTION

In accordance with the present invention there is provided a method for converting 2-methyl-1-butene to 2-methyl-2-butene which involves providing a hydrocarbon stream of isoamylenes including 2MB1 and 2MB2 in a ratio within the range of 1:1 to 5, to which a tertiary alkyl ether is added to form a mixture which is passed at a temperature of less than 60° C. and a LHSV which favors isomerization over an acidic ion exchange resin catalyst to produce a reaction product including 2MB1, 2MB2, an ether, an alcohol and isoamylene dimer, preferably wherein the tertiary alkyl ether is a member selected from the group consisting of tertiary amyl methyl ether (TAME) and methyl tertiary butyl ether (MTBE), and most preferably wherein the alkyl tertiary ether is TAME. When TAME and MTBE are used, the alcohol in the reaction product is methanol (MeOH). The 2MB1 and 2MB2 are preferably present in the mixture in a ratio of about 1:5 and the mixture is preferably in a liquid phase. The temperature at which reaction is performed is below 60° C. and preferably within the range of 30° C. up to 60° C., and the LHSV is within the range of 1 to 30 hr$^{-1}$, preferably wherein the temperature is within the range of 33° C. to 55° C., and the LHSV is within the range of 5 to 15 hr$^{-1}$. It is preferred that at least 3% by weight TAME, preferably in the range of 5 to 10%, be present in the mixture which may also include members selected from the group consisting of alkanes, alkenes, and alkynes, and preferably wherein the mixture is essentially devoid of water and alcohol.

The present invention is also directed to a method for controlling the ratio of 2-methyl-2-butene (2MB2) to 2-methyl-1-butene (2MB1) wherein a feedstream is produced by passing a hydrocarbon stream including isoamylene in the vapor phase over an acid-treated clay catalyst to produce a reaction product including 2MB1, and 2MB2. The temperature at which the reaction is within the range of 100° C. up to 250° C., and more preferably within the range of 110° C. to 250° C. The hydrocarbon stream may also include TAME, in which case the reaction product will include unreacted TAME in addition to methanol (MeOH). If this is the case, the reaction product may be washed with water to remove the MeOH to produce the feedstream. The 2MB2 and 2MB1 are preferably present in the reaction product in a ratio of about 1 to 5:1. The feedstream may then be subjected to fractionating wherein an overhead fraction containing 2MB2 and 2MB1 in a ratio of preferably 1:1, but in any event less than the ratio of 2MB2 and 2MB1 in the feedstream, and a sidestream fraction consisting essentially of 2MB2 and 2MB1 in a ratio of between 6 to 12:1 are separated. It is preferred to recycle the overhead hydrocarbon fraction of isoamylene including 2MB2 and 2MB1 in a ratio of about 1:1 to the feedstream prior to introducing the feedstream into the cracking reactor in which the previously described reaction is performed.

In accordance with the present invention, a method is provided for controlling the ratio of 2-methyl-2-butene (2MB2) to 2-methyl-1-butene (2MB1) in isoamylenes which involves fractionating a feedstream containing isoamylenes including 2MB2 and 2MB1 in a ratio of about 2 to 5:1 to effect a separation between an overhead hydrocarbon fraction of isoamylene including 2MB2 and 2MB1 present in a ratio of about 1:1 and a sidestream hydrocarbon fraction consisting essentially of isoamylene including 2MB2 and 2MB1 present in a ratio between about 6 to 12:1, and recovering the sidestream hydrocarbon fraction, preferably wherein the ratio of 2MB2 and 2MB1 in the sidestream hydrocarbon fraction of isoamylene is about 9:1. The feedstream including isoamylene may include an alkyl tertiary ether, preferably selected from the group consisted of tertiary amyl methyl ether (TAME) and methyl tertiary butyl ether (MTBE) in addition to 2MB2 and 2MB1. The preferred ratio of 2MB2 and 2MB1 in the feedstream is about 5:1. The preferred alkyl tertiary ether is TAME. In the embodiment wherein TAME is present in the feedstream, the fractionation preferably effects a further separation of unreacted TAME from the feedstream as a bottoms fraction.

BRIEF DESCRIPTION OF THE DRAWINGS

FIG. 1 shows a schematic representation of a process for producing isoamylene containing a high ratio of 2-methyl-2-butene relative to 2-methyl-1-butene.

DETAILED DESCRIPTION

A major use of isoamylenes, i.e. 2-methyl-1-butene and 2-methyl-2-butene, is in the manufacture of tackifying resins, alkyl phenols and agricultural intermediates, with 2MB2 being the preferred isomer. As previously mentioned, however, it is often difficult to convert and then recover 2MB2 from 2MB1.

Conventional processes for doing so include isomerization reactions. Typically, isomerization reactions are catalyzed by an acidic ion exchange resin catalyst. Such a catalyst, however, have been found to be inoperable if only isoamylenes or a mixture of isoamylenes with other alkanes, alkenes, and alkynes, are passed over it. Although not wishing to be bound by any particular theory, it is believed that such components do not provide the required environment to bring the catalyst to the necessary state of solvation, i.e. swelling; thus, the resin catalyst is ineffective. Although it has been suggested to include alcohols and water to provide the necessary environment to render the catalyst operable, it has been found that alcohols tend to react with the isoamylenes to form ethers thereby resulting in a product loss. The presence of water causes solubility problems and also tends to react with the isoamylenes to form alcohol; thus, water is not a particularly desirable solvent.

The present invention is based in part on the discovery that the presence of ether with the isoamylenes provides the necessary environment for resin catalyst operability. Thus, one embodiment of the present invention is directed to a method for rendering acidic ion exchange resin catalysts operable in the isomerization reaction to convert 2MB1 to 2MB2. Although numerous ethers may be used to bring the catalyst to the required state of solvation, it has been discovered that tertiary amyl methyl ether (TAME) and methyl tertiary butyl ether (MTBE) are preferred, with TAME being most preferred.

In accordance with the present invention, therefore, TAME is introduced in a mixture with isoamylenes over the resin catalyst. The iscamylenes being subjected to the isomerization reaction normally contains 2MB2 and 2MB1 in a ratio of about 2:1. The mixture in a liquid phase is passed over the acidic ion exchange resin catalyst at temperatures below 60° C. and preferably within the range of 30° C. up to 60° C. and a LHSV within the range of about 1 to 30 hr$^{-1}$ based on an empty reactor volume. It has been discovered that more preferred results are achieved when the isomerization reaction is performed at a temperature within the range of 33° C. to 55° C. and a LHSV within the range of 5 to 15 hr$^{-1}$, wherein the level of TAME introduced with the isoamylene over the catalyst is present in the amount of 5% by total weight of the reactor feed. The resultant reaction product contains 2MB2 and 2MB1 in a ratio which approaches the equilibrium for the isomerization reaction, i.e. over 12:1 at the lower temperatures, down to about 11:1 at the higher temperature.

Catalysts which have been found to be suitable for use in this process of the present invention include cation exchange resins. A preferred catalyst for purposes of the present invention is a macroreticular sulfonic acid cation exchange resin, such as Amberlyst 15 (trademark) and the like.

As previously indicated, this process of the present invention is conducted at a preferred reaction temperature of about 30° C. up to 60° C., and more preferably within the range of 33° C. to 55° C. It has been found that such temperature ranges are critical to this process of the present invention. Lower temperatures have been found to be inefficient because reaction rates are too low and, therefore, larger reactors are required for commercial production. Higher temperatures, however, tend to result in more undesirable by products, particularly isoamylene dimer is product loss, and methanol which contributes to product contamination. Notwithstanding performing the reaction at lower temperatures, it has been found that a gradual catalyst activity loss may be experienced because low levels of diolefins, and particularly cyclopentadiene, tend to foul the catalyst, thereby reducing its activity. Therefore, although the equilibrium ratio of 2MB2 to 2MB1 within the range of about 12:1 may be achieved when the reaction is performed at 33° C. at LHSV=20 hr$^{-1}$ on fresh catalyst, it has been found that where a catalyst is used that had been running for extended periods of time, such as about 1 month, the reaction must be carried out at a temperature of about 45° C. to produce an equilibrium ratio of about 11:1.

As previously indicated, LHSV should be maintained within the range of about 1 to 30 hr$^{-1}$ and more preferably within the range of 5 to about 15 hr$^{-1}$, based on standard conditions and empty reactor volume.

The process of the present invention is most preferably practiced at a high enough pressure to maintain the hydrocarbon in the liquid phase, preferably subcooled. Pressures employed are 10 psig or higher depending on temperature, and preferably from about 20 to about 100 psig.

Therefore, by careful selection of operating conditions, i.e., minimizing temperature and maximizing LHSV, it has been found that the methanol and dimer formation can be minimized.

In contrast to the discovery of the present invention, attempts to isomerize a hydrocarbon feedstream containing isoamylene which did not include TAME were not successful in achieving a similarly high product 2MB2 to 2MB1 ratio even by raising the temperature to increase the rate of the isomerization reaction.

Although this process of the present invention has been described with respect to the isomerization of 2MB1 to 2MB2, it is believed that the isomerization reaction over acidic ion exchange resin catalyst can in general be improved by the presence of an ether, and may be applied to the isomerization of numerous hydrocarbon feed compositions. Thus, hydrocarbon feeds which may be suitable for purposes of this process of the present invention include feed streams containing 2MB1 and 2MB2 in a mixture with saturated hydrocarbons, other straight chain and branched olefins, and small amounts of certain diolefins. One example of such a feed is the naphtha fraction from a refinery catalytic cracking unit. It should be noted, however, that high levels of diolefins, and even low-levels in the case of cyclopentadiene, have been found to foul the cation exchange resin, reducing its activity, and therefore its ability to catalyze the isomerization reaction. U.S. patent application Ser. No. 885,528, filed July 14, 1986 commonly owned with the present application, the disclosure of which is hereby incorporated by reference thereto, addresses the control of levels of diolefins in such process streams.

This process of the present invention, carried out within the ranges as described herein before, is illustrated in the following example. The examples, adapted to the isomerization of 2MB1 to 2MB2, are presented as illustrative of the general applicability of the process to feed stocks previously discussed without being limitative of the invention.

EXAMPLE I

A hydrocarbon stream including TAME was isomerized in accordance with the previously discussed method under the operating conditions indicated below using a macroreticular highly cross-linked cation exchange resin catalyst at a temperature of 43° C.

TABLE I

| Component | Run Process Pressure psig - 90 Process Temperature °C. - 43 LHSV hr$^{-1}$ - 10 | |
|---|---|---|
| | Feed Stream | Effluent Composition |
| 2MB2:2MB1 | 67/21 wt % | 69/6 wt % |
| ratio | 3:1 | 12:1 |
| 2MB1 conversion | | 71% |
| By Product | | |
| dimer | | 13.8 wt % |
| MeOH | | 240 ppm |

The above example shows that at a temperature of 43° C. the presence of TAME effectively increases the 2MB2:2MB1 ratio and results with a high 2MB1 conversion.

EXAMPLE II

In contrast to the run described in Example I, attempts were made to isomerize a hydrocarbon stream not including TAME following the procedure otherwise in accordance with the present invention under the conditions indicated below using a macroreticular highly cross-linked cation exchange resin catalyst with the following results:

TABLE II

| Run | Conditions | | | 2MB2:2MB1 Ratio |
|---|---|---|---|---|
| | Temperature | Pressure | LHSV | |
| A$_1$ | 55° C. | 90 | 6 hr$^{-1}$ | 4.8:1 |

The above example shows by way of contrast with Example I that the presence of TAME is necessary in order to achieve a high 2MB2 to 2MB1 ratio, and that increasing the temperature at which isomerization is performed does not make up for the absence of TAME.

EXAMPLE III

The importance of the presence of TAME for purposes of the present invention was further borne out when TAME was subsequently added to the hydrocarbon stream processed in Example II.

TABLE III

| Run | Conditions | | | 2MB2:2MB1 Ratio |
|---|---|---|---|---|
| | Temperature | Pressure | LHSV | |
| A$_2$ (with TAME) | 55° C. | 90 | 6 hr$^{-1}$ | 11.1 |
| A$_3$ (with TAME) | 43° C. | 90 | 6 hr$^{-1}$ | 11.1 |

As shown, upon introducing TAME to the hydrocarbon stream being isomerized, the 2MB2 to 2MB1 ratio of the recovered product increased dramatically and was maintained independent of the temperature at which the reaction was performed.

EXAMPLE IV

The purpose of this example is to show that isomerization of hydrocarbon streams including TAME, as in Example I, is effectively performed at low temperatures and results with a reduced by-product production.

TABLE IV

| | Conditions | | | 2MB2:2MB1 | By-Products | |
|---|---|---|---|---|---|---|
| Run | Temperature | Pressure | LHSV | Ratio | dimer | MeOH |
| A4 | 32° C. | 90 | 10 hr$^{-1}$ | 12.8:1 | 3.5 wt % | 100 ppm |

Thus, the presence of TAME has been discovered not only as being necessary in the production of high ratios of 2MB2 to 2MB1 but also in permitting isomerization to proceed under conditions which yield a higher purity product.

To summarize, the foregoing test results evidence that the presence of TAME in the hydrocarbon stream result in a higher ratio of 2MB2 to 2MB1 in contrast to performing the isomerization with no TAME in the reactor feed wherein the product 2MB2 to 2MB1 ratio dropped rapidly despite raising the temperature from 43° C. to 55° C. Surprisingly, introducing a feedstream containing TAME at this time increased the 2MB2 to 2MB1 product ratio to about 11:1, and that when the temperature was subsequently reduced to 43° C., the 2MB2 to 2MB1 ratio remained at 11:1 or higher. Although not wishing to be bound by any particular theory, it is believed that a higher ratio of 2MB2 to 2MB1 was achieved at 43° C. than at 55° C. because equilibrium favors higher ratios at low temperatures. Thus, it has been unexpectedly discovered that when isomerizing a hydrocarbon stream containing TAME, better results were obtained at lower temperatures, i.e. isomerization performed at 32° C. resulted with a product having a high 2MB2 and 2MB1 ratio of 12.8 and small amounts of by products, i.e., 3.5 wt % dimer and 100 ppm MeOH.

In another embodiment of the present invention, a method is provided to produce TAME which may be used in the isomerization and fractionating embodiments of the present invention. In this embodiment, TAME is provided by first recovering isoamylenes from a C$_5$ hydrocarbon stream by reacting the hydrocarbon stream with methanol over an acidic catalyst. Suitable catalysts for this purpose include acidic cation exchange resin catalysts. The reaction is carried out preferably at a temperature within the range of 40° C. to 80° C. and a LHSV of 0.5 to 4. The catalyst converts the 2MB1 and the 2MB2 contained in this C$_5$ hydrocarbon stream to tert amyl methyl ether (TAME) which may subsequently be recovered from the hydrocarbon stream by distillation. The TAME may be used, as previously described, to provide the requisite environment for the isomerization catalyst, or may be converted to isoamylene, i.e., 2MB2 and 2MB1, and methanol over an acidic catalyst in the vapor phase in the subsequently described cracking process, in which case the methanol is removed from the isoamylene and unreacted TAME by washing with water prior to fractionating.

Another embodiment of the present invention is directed to admixing isoamylene with TAME feed to an ether cracking reactor.

More specifically, in this embodiment a feedstream including isoamylene, and optionally tertiary amyl methyl ether (TAME), for example produced in accordance with the above-described procedure or recycled from the distillation tower as described hereinbelow, is passed in the vapor phase through an acid-treated clay cracking catalyst to produce an effluent product stream exiting from the catalyst bed which contains isoamylene. The product stream may also include an alcohol corresponding to the alkyl radical, i.e. methanol, in addition to unreacted TAME, if TAME is initially introduced in the feedstream. The latter being the case, the alcohol is first removed from the product stream, for example by washing with water, before passing the washed stream which is predominantly isoamylene, i.e, 2MB1 and 2MB2, and unreacted TAME, to a fractionation column to further improve the purity of the isoamylene by separating an isoamylene fraction having a desired ratio of 2MB2 to 2MB1 as a sidestream.

The preparation of the ether, i.e., TAME from isoamylene and its subsequent disassociation according to the present process is an important characteristic of the present invention. As previously discussed, prior art separating isoamylene from hydrocarbon streams directly by fractionation, because of the closeness of the boiling points of the components, is extremely difficult and has been found to be even more so if extremely high purity isoamylene is desired. However, it has been discovered that if isoamylene is first reacted with C$_1$–C$_6$ alcohols, i.e., methanol, to form ethers, such as TAME, the TAME can be separated from the other C$_5$ components by an otherwise conventional distillation technique. Thus, when TAME is disassociated according to the present invention, extremely high purity isoamylene may be produced, i.e., isoamylene with very little of any other C$_5$ present and a high ratio of 2MB2 to 2MB1 within the range of 6 to 12:1.

As previously mentioned, the most preferred tertiary alkyl ether for this purpose is tertiary amyl methyl ether, i.e., TAME, although other tertiary amyl alkyl ethers may be used. Depending on the particular ether, the alcohol which is derived from the disassociation of the ethers may be ethanol, isopropanol, tertiary butanol and the like, although methanol results when TAME is processed.

Suitable catalysts and conditions used in the cracking step of this stage of the process are disclosed in U.S. Pat. No. 4,691,073 MICHAELSON, commonly owned with this application, the disclosure of which is hereby incorporated by reference thereto. Briefly, the catalyst utilized in the present invention may be prepared by reacting a naturally occuring or synthetic clay with hydrofluoric acid (HF) or hydrochloric acid (HCl) followed by calcining. The reacting or incorporation of HF or the HCl with the clay can be accompanied by any means, such as contacting the clay with anhydrous HF or HCl or by impregnation of the clay with an aqueous acid, for example, a mixing method equilibrium absorption method, evaporation-to-dryness method, spray drying and the like. Preferably the clay is reacted with 1.0 to 70 wt %, preferably 20 to 50 wt % hydrofluoric acid or 1.0 to 30% to 37%, preferably 20 to 30 wt % hydrochloric acid at temperatures of 0° C. to 50° C., preferably 10° C. to 30° C. for 30–120 minutes. The amount of the acid is 0.001 to 1.0, and preferably 0.01 to 0.10gm anhydrous acid/gram clay. Following the reaction, the fluid is decanted and the clay is then preferably washed first with water and then with alcohol before calcining. The calcining temperature is selected so as to achieve a highly active high-surface area catalyst of a moisture content of less than 5 wt %. Preferably temperatures are 250° C. to 1,000° C., and more preferably 400° C. to 700° C. The calcination is generally carried out in air, but an atmosphere of an inert gas, for example nitrogen, carbon dioxide, and argon, in addition to steam or mixtures thereof may also be used. The time for calcination is generally 0.1 to 24 hours, and preferably 0.5 to 10 hours, although the time depends upon the calcination temperature. The amount of the flourine or chlorine compounds supported on the carrier is 0.1 to 100 parts by weight of the carrier and preferably 1.5% to 6.0%. Examples of the carrier containing silicon oxides include silica, montmorillonite, kaolinite, attapulgite, bentonite and acid clay, in addition to silica alumina, silica-zirconia, silica-magnesia and their mixtures. The silica may be either in the form of the gel or sol. A particularly preferred carrier is one prepared from attapulgite or montmorillonite-type minerals. The surface area of the carrier is preferably more than $1_m{}^2/gm$, and more preferably above $40_m{}^2/gm$. Preferred surface areas after calcination are in the range of $100_m{}^2/gm$ to $400_m{}^2/gm$.

The reaction of decomposition of the tert-alkyl ethers takes place with good yields under atmospheric pressures, but it is preferred to operate under slightly superatmospheric pressures so as to permit the use of cooling water without any other expedient to carry out the condensation of the products which are obtained.

The working pressures are generally ranging from 1 to 20 kilograms/sq.cmm absolute; and preferably under a pressure which is at least. equal to the vapor pressure of isoamylenes and TAME at the condensation temperature which is foreseen.

The reaction is carried out at a temperature below 250° C., and preferably in the range of 100° C.–250° C., and more preferably in the range of 110° C. –230° C. The reaction is carried out at a spacial velocity, expressed in terms of volume of liquid per volume of catalyst per hour (LHSV) ranging between 0.5 and 30, and preferably of 1 to 5. Preferably, conditions are selected to obtain conversions of the isoamylenes and tert-alkyl ethers of 80% and preferably 90%. With this in mind, the normal operating temperature of the cracker reactor should be maintained within the range of 120° F. to 170° F.

Thus the feedstream may also be obtained via decomposition of TAME as described in U.S. Pat. No. 4,691,073, and controlling the TAME conversion such that the desired amount of TAME remains in the isoamylene stream after water Washing to remove methane. Alternatively, a $C_5$ hydrocarbon stream containing isoamylenes may be reacted with methanol over an acidic catalyst to convert 2MB1 and 2MB2 to TAME for use in forming the mixture.

Referring now to FIG. 1, a schematic system is shown, which can be used to produce high purity isoamylene.

A feed stream 10 containing 90 wt % tertiary amyl methyl ether (TAME) is introduced together with isoamylene through feed stream 12 to a cracking reactor 14. As illustrated, the isoamylenes and TAME may be recycled from distillation column 20 as top and bottom fractions, respectively, to make up at least a portion of feedstreams 12 and 10. Alternatively or additionally, isoamylenes and TAME may be provided from a separate source of supply. For example, the TAME may be recovered from a $C_5$ hydrocarbon stream by reacting the $C_5$ hydrocarbon stream with methanol over an acidic catalyst to convert the 2-methyl-1-butene and the 2-methyl-2-butene contained in the $C_5$ hydrocarbon stream to tert-amyl methyl ether (TAME), as described above.

The cracking reactor 14 is provided with an acid-treated clay catalyst, as previously described herein, and is heated to a temperature within the range of 120° C. to 170° C. The effluent or product stream leaving the cracking reactor is composed of isoamylenes, i.e. 2MB1 and 2MB2, in a ratio of between 1:2 to 5 and preferably in a ratio of 1:5, unreacted TAME, and methanol (MeOH). The product stream is then washed with water to separate the methanol from the isoamylene and unreacted TAME in water wash stage 16. The resultant feedstream for the distillation column consists essentially of isoamylene, i.e. 2MB1 and 2MB2 in a ratio between 1:2 to 5 and preferably 1:5, and unreacted TAME and is then fed to a distillation column 20 which is preferably operated to vaporize the isoamylene. The vaporized overhead 22 is composed of isoamylene including 2MB1 and 2MB2 in a ratio which is less than the ratio of 2MB1 to 2MB2 in the feedstream and preferably about 1:1 which, as previously mentioned, is recycled through line 12a to be reintroduced to the cracking reactor 14 in feedstream 12. In accordance with the present invention, however, a side stream 24 is drawn off which consists essentially of isoamylene including 2MB1 and 2MB2 in a ratio of 1:9. The unreacted TAME is then withdrawn as a bottoms fraction 26 and either recycled through line 10a to be reintroduced to the cracking reactor 14 in feedstream 10, or may be used to provide the necessary environment for resin catalyst operability in the previously described isomerization reaction for converting 2MB1 to 2MB2.

EXAMPLE II

A feedstream of isoamylene with a 2MB2 to 2MB1 ratio of 1:1 in addition to TAME was fed in the gas phase to a reactor containing an acidic cracking catalyst, as described above, operated at 125° C. The reactor outlet ratio of 2MB2 to 2MB1 was increased as shown below:

| Component | Feed Stream | Reactor effluent |
|---|---|---|
| Isoamylene/TAME | 36/64 wt % | 76/2 wt % |
| 2MB2:2MB1 | 18/18 wt % | 51/25 |
| 2MB2 to 2MB1 ratio | 1:1 | 2:1 |

Computer simulations using fractionation design computer programs were used based on the reactor product composition from the above test as the feed to a distillation tower, to determine a design of a distillation tower that would separate this reactor products into three streams: a bottoms product consisting mainly of the unreacted TAME; an overhead stream consisting of isoamylene in a 2MB2 to 2MB1 ratio of 1:1; and a high purity isoamylene sidestream with a 2MB2 to 2MB1 ratio of 6:1 or higher.

It is further understood that although the invention has been specifically described with reference to particular means and embodiments, the foregoing description is that of preferred embodiments of the invention. The invention, however, is not limited to the particulars disclosed but extends to all equivalents, and various changes and modifications may be made in the invention without departing from the spirit and scope thereof.

What is claimed is:

1. The method for converting 2-methyl-1-butene to 2-methyl-2-butene comprising:
   providing a hydrocarbon stream comprising isoamylene including 2-methyl-1-butene and 2-methyl-2-butene in a ratio within the range of 1:1 to 5;
   adding a tertiary alkyl ether to said isoamylene to form a mixture;
   passing said mixture of isoamylene and tertiary alkyl ether which is essentially devoid of water at a temperature within the range of 30° C. up to 60° C. and an LHSV within the range of 1 to 30 $hr^{-1}$ over an acidic ion exchange resin catalyst to produce a reaction product including 2-methyl-1-butene, 2-methyl-2-butene an ether, and an alcohol wherein said 2-methyl-2-buten and 2-methyl-1-butene are present in said reaction product in a ratio of 6 to 12:1.

2. The method in accordance with claim 1, wherein said tertiary alkyl ether is a member selected from the group consisting of tertiary amyl methyl ether and methyl tertiary butyl ether.

3. The method in accordance with claim 2, wherein said the tertiary alkyl ether is tertiary amyl methyl ether and said alcohol is methanol.

4. The method in accordance with the claim 3 wherein said mixture is in a liquid phase.

5. The method in accordance with claim 4, wherein said temperature is within the range of 33° C. to 55° C., and the LHSV is within the range of 5 to 15 $hrs.^{-1}$.

6. The method in accordance with claim 5, wherein said mixture comprises at least 3% by total weigh tertiary amyl methyl ether.

7. The method in accordance with claim 6 wherein said TAME contained in the mixture is preferably in the range of 5 to 10% by total weight.

8. The method in accordance with claim 7, wherein said mixture comprises members selected from the group consisting of alkanes, alkenes, and alkynes.

9. The method in accordance with claim 8, wherein said mixture is essentially devoid of alcohols.

10. A method of converting 2-methyl-1-butene to 2-methyl-2- butene comprising:
    providing a hydrocarbon stream comprising isoamylene;
    passing said hydrocarbon stream at a temperature of from 100° C. to 250° C. over an acid-treated clay catalyst to form a resultant stream comprising 2-methyl-2-butene and 2-methyl-1-butene in a ratio of 1 to 5:1.

11. The method in accordance with claim 10, wherein said acid is a member selected from the group consisting of hydrofluoric acid and hydrochloric acid, and mixtures of HF and HCl.

12. The method in accordance with claim 11, wherein said catalyst is prepared by reacting a clay with said acid, followed by calcining.

13. The method in accordance with claim 10, wherein said clay is a natural clay.

14. The method in accordance with claim 12, wherein said clay is selected from he group consisting of attapulgus clay and montmorillonite clay.

15. The method in accordance with claim 10 comprising fractionating a feedstream comprising said 2-methyl-2-butene and 2-methyl-1-butene in a ratio of 1 to 5:1 to effect a separation between an overhead hydrocarbon fraction of isoamylene including 2-methyl-2-butene and 2-methyl-1-butene and a sidestream fraction consisting essentially of 2-methyl-2-butene and 2-methyl-1-butene in a ratio of 6 to 12:1.

16. The method in accordance with claim 15, comprising recycling said overhead hydrocarbon fraction of isoamylene to said hydrocarbon stream.

17. The method in accordance with claim 15 wherein said sidestream fraction consists essentially of 2-methyl-2-butene and 2-methyl-1-butene in a ratio of about 6 to 9:1.

18. The method in accordance with claim 17, wherein said sidestream fraction consists essentially of 2-methyl-2-butene and 2-methyl-1-butene in a ratio of 9:1.

19. The method in accordance with claim 15, wherein said hydrocarbon stream further comprises tertiary amyl methyl ether, and said resultant stream comprises a tertiary ether and an alcohol.

20. The method in accordance with claim 19, wherein said tertiary ether is a tert-amyl-methyl-ether.

21. The method in accordance with claim 20, wherein said resultant stream comprises tertiary amyl methyl ether and methanol.

22. The method in accordance with claim 21 comprising washing said resultant stream in forming said feedstream.

23. The method in accordance with claim 22, wherein said feedstream further comprises tertiary amyl methyl ether.

24. The method in accordance with claim 23, wherein said fractionating effects a separation of unreacted tertiary amyl methyl ether as a bottoms fraction.

25. The method in accordance with claim 24, comprising recycling said bottoms fraction of tertiary amyl methyl ether to said hydrocarbon stream.

26. The method in accordance with claim 15, wherein said ratio of 2-methyl-2-butene and 2-methyl-1-butene in said feedstream is about 2 to 5:1.

27. The method in accordance with claim 10, wherein said hydrocarbon stream is in a vapor phase.

28. The method in accordance with claim 15, wherein said temperature is within the range of 120° C. to 170° C.

29. The method in accordance with claim 22, wherein said washing removes said methanol to produce said feedstream.

30. The method in accordance with claim 24 comprising recycling said unreacted tertiary amyl methyl ether to form said hydrocarbon stream.

31. The method in accordance with claim 16, wherein said overhead hydrocarbon fraction of isoamylene comprises 2-methyl-2-butene and 2-methyl-1-butene in a ratio of about 1:1.

* * * * *